United States Patent [19]

Quick

[11] 4,454,141
[45] Jun. 12, 1984

[54] TRANS-B/C-7-(1-HYDROXYPENTYL)-3-METHOXY-17 METHYL-6,7-DIDEHYDROMORPHINANS, AND METHODS OF RELIEVING PAIN WITH THEM

[75] Inventor: James E. Quick, Lexington, Mass.

[73] Assignee: SISA Pharmaceutical Laboratories, Inc., Cambridge, Mass.

[21] Appl. No.: 422,218

[22] Filed: Sep. 23, 1982

[51] Int. Cl.³ .................. A61K 31/485; C07D 221/28
[52] U.S. Cl. ..................................... 424/260; 544/260
[58] Field of Search ........................... 546/74; 424/260

[56] References Cited

U.S. PATENT DOCUMENTS 3,166,560  1/1965  Sawa et al. ........................... 546/74
4,347,361  8/1982  Quick et al. ........................... 546/45
4,374,139  2/1983  Mohacsi ................................ 424/260

OTHER PUBLICATIONS

Bentley et al., *Journal of the American Chemical Society*, 89:13, pp. 3267–3273.

Primary Examiner—Donald G. Daus
Assistant Examiner—Diana G. Rivers
Attorney, Agent, or Firm—Jerome L. Jeffers

[57] ABSTRACT

Disclosed are trans-B/C-7-(1-hydroxypentyl)-3-methoxy-17-methyl-6,7-didehydromorphinans of the formula:

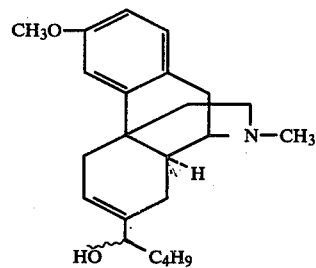

These compounds have been found to possess potent analgesic activity.

6 Claims, No Drawings

TRANS-B/C-7-(1-HYDROXYPENTYL)-3-METHOXY-17 METHYL-6,7-DIDEHYDROMORPHINANS, AND METHODS OF RELIEVING PAIN WITH THEM

BACKGROUND OF THE INVENTION

Certain well-known narcotic analgesics belong to the class of 4,5α-epoxymorphinan compounds which have the following basic ring system in which the atoms are numbered as indicated:

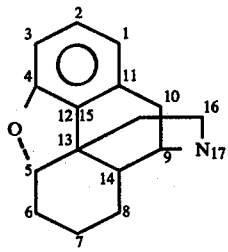
(I)

The two most familiar compounds of this class are morphine and its 3-methyl ether, codeine, with the structures indicated below:

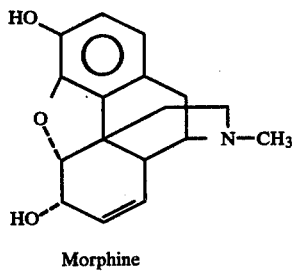

Morphine (II)

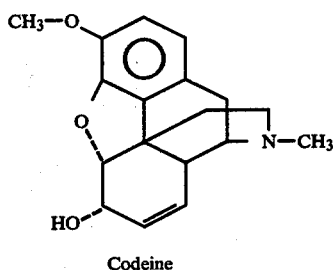

Codeine (III)

When the 6-hydroxyl group of each of these compounds is oxidized to an oxo group, the compounds conveniently are referred to as morphinone and codeinone, respectively. When the N-methyl groups of the latter compounds are replaced by other substituent groups they may be referred to as N-substituted normorphinones and norcodeinones, respectively. There are two types of nomenclature commonly used for describing compounds herein. The trivial names, such as morphine or morphinone, are widely accepted and used for the sake of brevity and clarity. The Chemical Abstracts nomenclature is preferred and is used wherever precision is needed.

Compounds having the basic morphine or morphinan nucleus, either with or without the 4,5α-epoxy bridge, are of interest because they may act as strong analgesics, and research into this class of compounds continues in laboratories throughout the world.

Bentley and Hardy disclose in *Journal of the American Chemical Society*, 89:13, Pp. 3267–73, certain Diels-Alder adducts of thebaine having the formula:

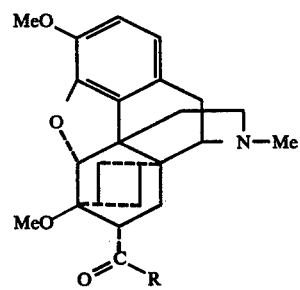

where R is methyl or phenyl. It is stated that these compounds possess analgesic activity. This 6,14-endoethenotetrahydrothebaine (oripavine) series of analgesics, as disclosed by Bentley and his coworkers, differs from the compounds of the present invention by the presence of the 6,14-etheno bridge in the oripavines which alters the stereochemistry of the molecules. Furthermore, while both are substituted at the 7-position, the oripavines contain a methyl ether of a tertiary alcohol at C-6 whereas the present compounds are unsubstituted at the 6-position and contain a double bond at $C_6$-$C_7$.

U.S. Pat. No. 4,347,361 (issued Aug. 31, 1982) discloses 4,5α-epoxy-3-methoxy-7-(1-hydroxyalkyl)-morphinan-6-one compounds of the formula:

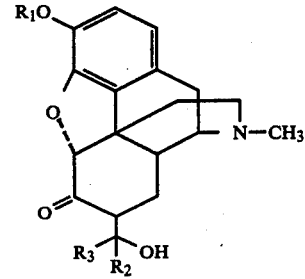

where $R_1$ is H or methyl, $R_2$ is straight or branched chain alkyl of from 1 to 10 carbon atoms, aryl, substituted aryl or arylalkyl and $R_3$ is a straight chain alkyl group of 1 to 4 carbon atoms. These compounds differ from those claimed herein in several respects including the presence of a 1-tertiary alcohol rather than a 1-secondary alcohol at the 7-position.

SUMMARY OF THE INVENTION

Disclosed are 6,7-didehydro-7-(1-hydroxy-pentyl)-3-methoxy-17-methyl-14α-morphinans of the formula:

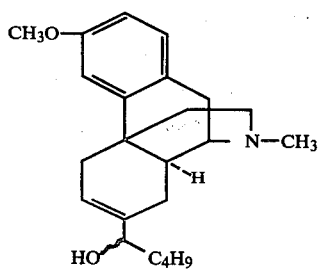

In this formula the OH group can be in the alpha position (projecting below the plane of the molecule) or in the beta position (projecting above the plane of the molecule).

DESCRIPTION OF THE INVENTION

The method of preparing the compounds disclosed and claimed herein is set out in the following scheme I. According to scheme I, the known 3-methoxy-17-methyl-14α-morphinan-6-one (1) described by Sawa, et al in *Tetrahedron*, 21, 1133 (1965) is converted to the α,β-unsaturated aldehyde (4). The ketone (1) was heated with dimethylformamide dimethylacetal under the conditions disclosed by Abdulla, et al. in *J. Org. Chem.*, 43, 4248 (1978) to give the dimethylaminomethylene ketone (2). Without purification, compound (2) was treated with butanethiol and p-toluenesulfonic acid in refluxing benzene [Martin, et al., *Tet. Lett.*, 4459 (1976)] to give the corresponding n-butylthiomethylene ketone (3). Reduction of crude (3) with sodium borohydride in methanolic sodium hydroxide solution, followed by acid hydrolysis, as described by Bernstein, in *Tet. Lett.*, 1015 (1979) and Church, et al., *J. Org. Chem.*, 27, 1118 (1962) afforded the α,β-unsaturated aldehyde (4) which was purified by column chromatography. Treatment with n-butyllithium in tetrahydrofuran at −68° C. gave (5), a mixture of diastereomers which were separated by column chromatography.

SCHEME I

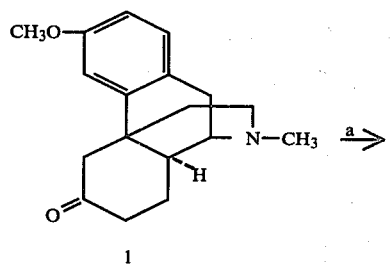

1

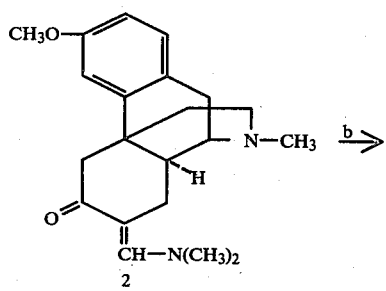

2

-continued
SCHEME I

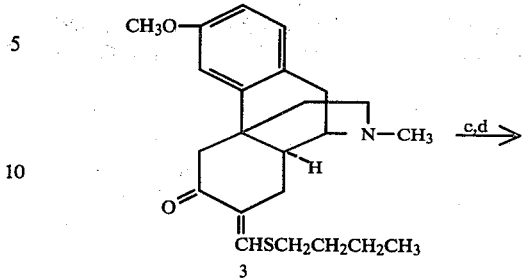

3

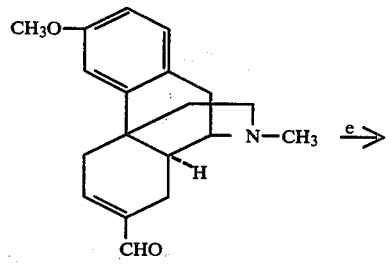

4

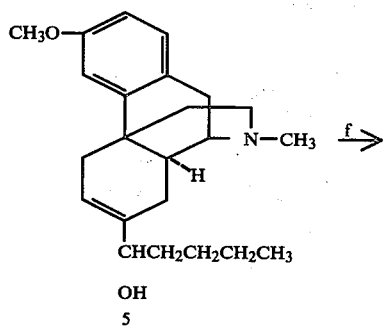

5

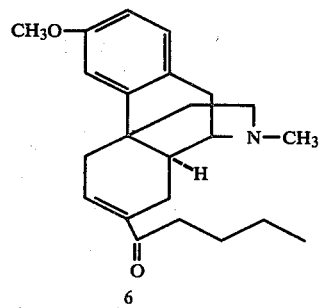

6 a: H₂CN(CH₃)₂, heat
   CH₃O   OCH₃
b: CH₃CH₂CH₂CH₂SH, benzene, p-toluenesulfonic acid, heat
c: NaBH₄, NaOH, CH₃OH, H₂O
d: dilute H₂SO₄, heat
e: CH₃CH₂CH₂CH₂Li, THF, −68° C.
f: Sodium borohydride/CH₃OH The synthesis of these compounds is further illustrated by the following examples:

EXAMPLE I

A. Trans-B/C-7-formyl-3-methoxy-17-methyl-6,7-didehydromorphinan (4).

A solution of 3-methoxy-17-methyl-14-α-morphinan-6-one (1) (5.8 g, 0.02 mol) in dimethylformamide dimethylacetal (31 g, 0.26 mol) was heated at 130° C. for 20 hours, then it was cooled and concentrated in vacuo to give (2). NMR δ2.38 (s, ~3H, N—CH₃), 3.17 (s, ~6H, N (CH₃)₂), 3.78 (s, 3H, OCH₃), 6.8-7.2 (m, 3H, aryl), 7.67 (s, 1H,=CH~N). A solution of the crude residue in benzene (100 ml) was heated at 80° C. with butanethiol (4.5 ml, 0.04 mol) and p-toluenesulfonic acid monohydrate (20 mg) for 27 hours. The cooled solution was washed with aqueous sodium bicarbonate solution, dried (Na₂SO₄) and concentrated. A methanol (200 ml) solution of the crude butylthiomethylene derivative (3) was treated with sodium borohydride (5 g) in 0.25 N sodium hydroxide (40 ml). After 3 hours the solution was acidified with 10% sulfuric acid and heated at reflux for 1.5 hours. After basification with ammonium hydroxide, extraction with chloroform, drying (Na₂SO₄), and concentration, a brown oil was obtained. Chromatography (silica gel, chloroform methanol mixtures) of that oil afforded pure (4) (3.4 g, 56% yield). NMR δ0.9-1.3 (m, 1H,), 1.7-3.4 (m's), 2.33 (s, ~3H, N-CH₃), 3.80 (s, 3H, OCH₃), 6.7-7.2 (m, 4H, aryl and vinyl), 9.57 (s, 1H, CHO); ir 1675 cm⁻¹; ms 297 (32,M⁺), 268 (7, M⁺—CHO), 59 (49), 43 (100). Hydrochloride (ethanol) mp 210° C. (decomp.)

Anal: ($C_{19}H_{23}NO_2 \cdot HCl \cdot 0.5\ H_2O \cdot 0.5\ C_2H_5OH$), C, H, N, Cl. Calcd: C, 65.64; H, 7.73; N, 3.83; Cl, 9.69. Found: C, 65.96; H, 7.61; N, 3.87; Cl, 9.76.

B. Trans-B/C-7-(1-hydroxypentyl)-3-methoxy-17-methyl-6,7-didehydromorphinan (5).

A solution of (4) (500 mg, 1.7 mmol) in THF (70 ml) was treated with n-butyllithium (5 mmol) at −68° C. After 1 hour the mixture was quenched with aqueous ammonium chloride solution, diluted with water, and extracted with chloroform. The organic layers were dried and concentrated. The product was chromatographed (silica gel, chloroform-methanol mixtures) to afford diastereomers (5a) (MLS-5678) OH in the alpha position (35% yield) and (5b) (MLS-5679) OH in the beta position (30% yield).

The assignment of the OH group to the β-position in 5b and to the α-position in 5a is based on the following reasoning: Both diastereomeric alcohols, 5a and 5b, are oxidized to the same ketone 6. Reduction of 6 with sodium borohydride in methanol provides the same mixture of alcohols in unequal amounts. The major product was found to be 5b. From inspection of the model of 6, it appears that the cisoid rotamer would be more stable than the transoid rotamer because of the proximity of the vinyl proton to the α-protons in the latter. In the cisoid rotamer, approach of H⁻ from the β-side is hindered by the C-8 axial proton and is, therefore, unfavored. Approach of H⁻ from the α-side is more likely, and leads to an alcohol with OH in the β-position. In the transoid form of 6, there is no preference for attack at one side or the other. The major product 5b from reduction of 6 should, therefore, be the diastereomer in which the hydroxyl group is in the β-configuration.

5a: NMR δ0.8-3.1 (m's), 2.37 (s, ~3H, NCH₃), 3.78 (s, 3H, OCH₃), 4.1 (br t, 1H, >CHOH), 5.7 (m, 1H, vinyl), 6.6-7.1 (m, 3H, aryl); ir (film) 3400 cm⁻¹; MS 355 (100,M⁺), 340 (18,M⁺—CH₃), 338 (25, M⁺—OH), 337 (15, M⁺—H₂O), 298 (77, M⁺—C₄H₉), and 268 (40, M⁺—CH(OH)C₄H₉).

Anal. ($C_{23}H_{34}NO_{2.5}$), C, H, N. Calcd: C, 75.77; H, 9.42; N, 3.54. Found: C, 73.55; H, 9.42; N, 3.45.

5b: NMR δ0.8-3.4 (m's), 2.47 (s, ~3H, NCH₃), 3.82 (s, 3H, OCH₃), 4.1 (br t, 1H, >CHOH), 5.7 (m, 1H, vinyl), 6.7-7.2 (m, 3H, aryl); ir (film) 3400(br)cm⁻¹; MS 355, (100, M⁺), 340 (18, M⁺—CH₃), 338 (26, M⁺—OH), 337 (12, M⁺—OH), 298 (66, M⁺—C₄H₉), 268 (36, M⁺—CH(OH)C₄H₉).

Anal. ($C_{23}H_{35}NO_3$), C, H, N. Calcd: C, 73.94; H, 9.46; N, 3.75. Found: C, 73.55; H, 9.42; N, 3.45.

The IR spectra of 5a and 5b were almost identical. The NMR spectra showed different shapes in the methylene multiplets.

PHARMACOLOGICAL EVALUATION

The present compounds were found to possess particularly potent analgesic effects upon mice in the acetic acid writhing test which was carried out in the following manner:

ACETIC ACID MOUSE WRITHING TEST

The analgesic effects of test compounds were determined in mice by use of the acetic acid writhing test described by B. A. Whittle, *Brit. J. Pharmacol.*, 22: 246 (1964). In this test at least 3 groups of 5 male CD-1 mice each were given subcutaneous doses of the test drug dissolved in either distilled water or distilled water acidified with HCl depending on the solubility of the compound. Fifteen (15) minutes post drug, 0.4 milliliter of a 0.75% or 1.0% or 0.6 milliliter of a 1.0% V/V acetic acid in distilled water solution was administered intraperitoneally. The number of writhes in a 20 minute interval begining 5 minutes after the acetic acid injection was determined and compared with the number of writhes in control groups which had received only acetic acid.

Percent inhibition of writhing was calculated as:

$$\%\ \text{inhibition} = \frac{\text{No. control writhes} - \text{No. treated writhes}}{\text{No. control writhes}} \times 100$$

The ED₅₀ dose, i.e., the dose required to reduce the number of writhes by 50%, was determined graphically from a plot of % inhibition as a probit versus log dose. Confidence limits of 95% were calculated on the basis of those results falling in the range 16-84% inhibition. See Lichtfield, J. T. and Wilcoxon, F., *J. Pharmacol. Exp. Ther.*, 96:99, (1949).

Using this procedure, MLS-5678 was found to have an ED₅₀ of 0.0058 mg/kg and MLS-5679 was determined to have an ED₅₀ of 0.0062 mg/kg.

The rat tail flick test for analgesia was also carried out with these compounds. This test was carried out as follows:

At least 3 groups of 5 male Wistar rats (100-120 g) were used for this study. Two control reaction times were determined 30 minutes apart by exposing the rat's tail to a focused source of light, connected to a timer. Removal of the tail away from the source of light activates a cut off switch which records the reaction time on a digital readout. The test drug was administered subcutaneously and 20 minutes later the reaction time was redetermined. A 10 second cut off time was used.

The percent response was calculated from the following formula:

$$\%\ \text{effect} = 100 \times \frac{\text{test reaction time} - \text{control reaction time}}{10 - \text{control reaction time}}$$

The ED₅₀ dose, i.e., the dose required to increase the control reaction time to 50% of the difference between the control reaction time and 10 seconds, was determined graphically from a plot of % effect as a probit versus log dose. Confidence limits of 95% were calculated on the basis of those results falling in the range 16–84% inhibition. See Lichtfield, J. T. and Wilcoxon, F., *J. Pharmacol. Exp. Ther.*, 96, 99 (1949).

Using this procedure, MLS-5678 was found to have an $ED_{50}$ of 0.3 mg/kg and MLS-5679 was determined to have an $ED_{50}$ of 1.8 mg/kg.

The analgesic potency of these compounds is compared to morphine which exhibits an $ED_{50}$ of 0.79 mg/kg in the mouse writhing test and $ED_{50}$ of 7.32 mg/kg in the rat tail flick test.

The compounds of the present invention form pharmacologically acceptable addition salts with organic and inorganic acids. Typical acid addition salts are the tartrate, hydrobromide, hydrochloride, and maleate. The hydrochloride is preferred. These compounds are useful in relieving moderate to severe pain in an individual for whom such therapy is indicated. The term individual means a human being or an experimental animal that is a model for a human being. The dose to be administered to achieve the desired result, i.e., the effective dose, may vary from individual to individual but is readily determined by one skilled in the art without undue experimentation. These compounds may be administered by known methods of therapeutic administration such as intravenous, parenteral, buctal, rectal, and oral. Dosage forms for the administration of these compounds can be prepared by methods recognized in the pharmaceutical sciences.

What is claimed is:

1. Trans-B/C-7-(1-hydroxypentyl)-3-methoxy-17-methyl-6,7-didehydromorphinans of the formula:

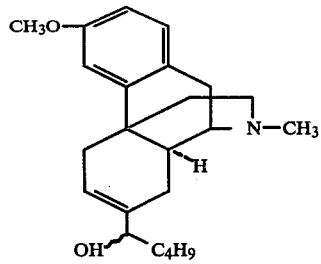

2. A compound as defined by claim 1 wherein the hydroxyl group is in the alpha configuration.

3. A compound as defined by claim 1 wherein the hydroxyl group is in the beta configuration.

4. A method of relieving pain in an individual requiring such treatment which comprises administering to such individual an analgesically effective amount of a compound characterized by the formula in claim 1.

5. The method of claim 4 wherein the compound so administered has its hydroxyl group in the alpha configuration.

6. The method of claim 4 wherein the compound so administered has its hydroxyl group in the beta configuration.

* * * * *